United States Patent [19]

Houlihan

[11] Patent Number: 4,925,851

[45] Date of Patent: May 15, 1990

[54] 2- OR 4-SUBSTITUTED-[2-(1H-IMIDAZOL-1-YL)ETHYL]PIPERIDINES

[75] Inventor: William J. Houlihan, Mountain Lake, N.J.

[73] Assignee: Sandoz Pharmaceuticals Corp., E. Hanover, N.J.

[21] Appl. No.: 355,956

[22] Filed: May 23, 1989

[51] Int. Cl.$^5$ .................. A61K 31/445; C07D 401/06
[52] U.S. Cl. ..................................... 514/326; 546/210
[58] Field of Search ....................... 514/326; 546/210

[56] References Cited

U.S. PATENT DOCUMENTS 3,714,158 1/1973 Hoff .................................... 546/210
4,537,969 8/1985 Wei et al. ........................... 546/210

Primary Examiner—Robert T. Bond
Attorney, Agent, or Firm—Gerald D. Sharkin; Robert S. Honor; Joseph J. Borovian

[57] ABSTRACT

The invention discloses certain 2- or 4-substituted-[2-(1H-imidazol-1-yl)ethyl]piperidines useful as anti-tumor agents, pharmaceutical compositions containing said compounds as an active ingredient thereof and a method of using such compositions in treating tumors.

17 Claims, No Drawings

2- OR 4-SUBSTITUTED-[2-(1H-IMIDAZOL-1-YL)ETHYL]-PIPERIDINES

The present invention relates to certain 2- or 4-substituted-[2-(1H-imidazol-1-yl)ethyl]piperidines and to their use as anti-tumor agents. The invention also relates to pharmaceutical compositions containing the aforementioned compounds as an active ingredient thereof and to the method of using such compositions for treating tumors.

Leukemia, as well as other malignancies of unknown origin including ascitic tumors, has occupied the attention of research organizations for many years and until most recently without appreciable success. Today, many types of tumors can be effectively treated with drugs. In this connection, U.S. Pat. No. 4,119,714 discloses certain etherlysolecithins useful in influencing and controlling the interfacial properties of cell membranes, U.S. Pat. No. 4,393,052 discloses novel anthracycline glycosides useful in treating certain tumors, U.S. Pat. No. 4,393,064 discloses the use of 10-deazaminepterin in treating leukemia and ascitic tumors, U.S. Pat. No. 4,396,553 is directed to tetrahydronaphthalene and indane compounds which are useful as tumor inhibiting agents and U.S. Pat. No. 4,426,525 discloses certain tridecyloxy or tetradecyloxy propane derivatives useful in inhibiting the multiplication of tumor cells. In addition, Belgian Patents 854,269 and 854,270 disclose anti-tumor lysolecithin compositions effective against Ehrlich's Ascites methylcholanthrene-induced tumors and myelomas.

The essence of the present invention is the discovery that certain 2- or 4-substituted-[2-(1H-imidazol-1-yl)ethyl]piperidines of formula I:

$$R-N\underset{\underset{4}{\phantom{X}}}{\overset{2\phantom{X}3}{\phantom{X}}}\phantom{X}CH_2CH_2-N\overset{\phantom{X}}{\underset{R_1}{\phantom{X}}}\phantom{X}\!\!\!\!=\!\!N \qquad I$$

wherein
R is a group selected from $$-CH_2\!-\!\!(CH_2)_{\overline{m}}CH_3,$$

$$-\overset{O}{\underset{\|}{C}}\!-\!\!(CH_2)_{\overline{m}}CH_3 \text{ and}$$

$$-\overset{O}{\underset{\|}{C}}-\overset{R_2}{\underset{\underset{CH_3}{|}}{C}}-CH_3,$$

where m is an integer 2 to 18 and $R_2$ is hydrogen or methyl; and
$R_1$ is $-(CH_2)_{\overline{n}}R_3$, where n is 0 or an integer 1 to 13, and $R_3$ is hydrogen, i-propyl or t-butyl, and the floating group is in the 2- or 4-position, with the provisos that: (1) the sum of the carbon atoms in $R_1$ does not exceed 13; and (2) the sum of the carbon atoms in R and $R_1$ does not exceed 25;
and their pharmaceutically acceptable acid addition salts, are useful as anti-tumor agents.

Of the compounds of formula I, preferred are the compounds of formula I':

$$R'-N\underset{\underset{4}{\phantom{X}}}{\overset{2\phantom{X}3}{\phantom{X}}}\phantom{X}CH_2CH_2-N\overset{\phantom{X}}{\underset{R_1'}{\phantom{X}}}\phantom{X}\!\!\!\!=\!\!N \qquad I'$$

wherein
R' is a group selected from $$-CH_2\!-\!\!(CH_2)_{\overline{m'}}CH_3,$$

$$-\overset{O}{\underset{\|}{C}}\!-\!\!(CH_2)_{\overline{m'}}CH_3 \text{ and}$$

$$-\overset{O}{\underset{\|}{C}}-\overset{R_2}{\underset{\underset{CH_3}{|}}{C}}-CH_3,$$

where m' is an integer 4 to 16 and $R_2$ is as defined above; and
$R_1'$ is $-(CH_2)_{\overline{n'}}R_3$, where n' is 0 or an integer 1 to 11, and $R_3$ is as defined above, and the floating group is in the 2- or 4-position, with the provisos that: (1) the sum of the carbon atoms in $R_1'$ does not exceed 11; and (2) the sum of the carbon atoms in R' and $R_1'$ is between 15 and 25;

and their pharmaceutically acceptable acid addition salts, where such may exist.

The more preferred compounds of formula I are those of formula I' wherein R' and $R_1'$ are as defined above, with the provisos that: (1) the sum of the carbon atoms in $R_1'$ does not exceed 11; and (2) the sum of the carbon atoms in R' and $R_1'$ is between 15 and 20; and their pharmaceutically acceptable acid addition salts, where such may exist.

The compounds of formula I where R is a group $$-\overset{O}{\underset{\|}{C}}\!-\!\!(CH_2)_{\overline{m}}CH_3$$

or a group $$-\overset{O}{\underset{\|}{C}}-\overset{R_2}{\underset{\underset{CH_3}{|}}{C}}-CH_3$$

and $R_1$ is as defined above may be prepared by a three-step reaction as follows:

$$\underset{(II)}{HN\underset{\underset{4}{\phantom{X}}}{\overset{2\phantom{X}3}{\phantom{X}}}\phantom{X}CH\!=\!CH_2} + \underset{(III)}{HN\overset{\phantom{X}}{\underset{R_1}{\phantom{X}}}\phantom{X}\!\!\!\!=\!\!N} \xrightarrow[N_2 \text{ atm.}]{\text{acetic acid}}$$

-continued

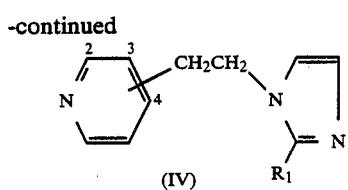

where $R_1$ is as defined above and the floating group is in the 2- or 4-position.

STEP 2

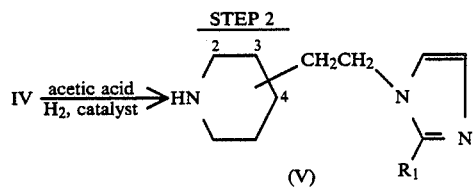

where $R_1$ is as defined above and the floating group is in the 2- or 4-position.

STEP 3

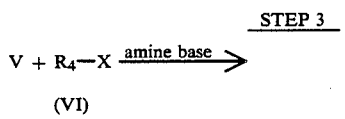

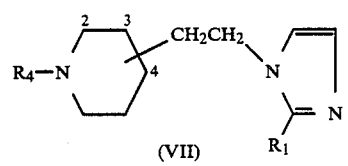

where $R_4$ is

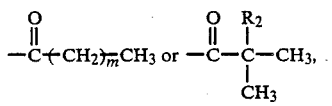

X is chloride or bromide, $R_1$ is as defined above and the floating group is in the 2- or 4-position.

With respect to the individual steps, Step 1 involves the reaction of a 2- or 4-vinylpyridine compound of formula II with an imidazole compound of formula III in the presence of glacial acetic acid and under a nitrogen atmosphere to yield a compound of formula IV. The reaction is typically carried out at a temperature of from 110° to 150° C. for a period of between 4 and 8 hours.

Step 2 involves the hydrogenolysis of a compound produced in Step 1, i.e., a compound of formula IV, by treating said compound with glacial acetic acid and a catalyst, e.g., palladium or platinum on carbon, platinum oxide, etc., and subjecting the resulting mixture to a pressure of between 20 and 75 lbs. of hydrogen gas at a temperature of from 20° to 40° C. to yield a compound of formula V.

In Step 3, a compound produced in Step 2, i.e., a compound of formula V, is reacted with an alkanoyl chloride or bromide of formula VI in the presence of an amine base, e.g. a tri-$C_{1-4}$alkylamine such as triethylamine, to yield a compound of formula VII. The reaction is typically carried out in the presence of an inert, organic solvent, e.g., an aliphatic hydrocarbon such as hexane, an aromatic hydrocarbon such as benzene or toulene, a cyclic ether such as tetrahydrofuran, or a mixture of such solvents, e.g., a mixture of toluene and tetrahydrofuran. As to reaction conditions, the reaction is typically carried out at a temperature of from $-20°$ to 30° C. for a period of between 5 and 72 hours.

The compounds of formula I where R is a group $-CH_2-(CH_2)_{\overline{m}}CH_3$ and $R_1$ is as defined above may be prepared by the following reaction employing a compound of formula VII as the starting material:

REACTION A

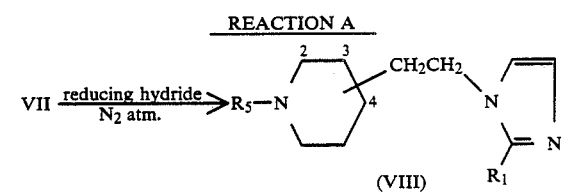

where $R_5$ is $-CH_2-(CH_2)_{\overline{m}}CH_3$, $R_1$ is as defined above and the floating group is in the 2- or 4-position.

In the above reaction, a compound of formula VII is reacted with a reducing hydrde, e.g., lithium aluminum hydride, under a nitrogen atmosphere to yield a compound of formula VIII. The reaction is generally carried out in an inert, organic solvent, e.g., a cyclic ether such as tetrahydrofuran, at reflux temperature for a period of between 4 and 10 hours.

The compounds of formula II, III and VI are either known and obtained by methods described in the literature, or where not known, may be obtained by methods analogous to those described in the literature.

The product of each reaction may, if desired, be purified by conventional techniques such as recrystallization (if a solid), column chromatography, preparative thin layer chromatography, gas chromatography (if sufficiently volatile) or fractional distillation under high vacuum (if sufficiently volatile). Often, however, the crude product of one reaction may be employed in the following reaction without purification.

As previously indicated, pharmaceutically acceptable acid addition salts (i.e., those salts which do not significantly increase the toxicity of the base compound) of the compounds of formula I, where such may exist, are included within the scope of this invention. These include salts of mineral acids such as hydrochloric, hydrobromic, phosphoric and sulfuric acids, as well as salts of organic acids such as tartaric, acetic, citric, malic, maleic, methanesulfonic and gluconic acids.

As indicated above, all of the compounds of formula I, and their pharmaceutically acceptable acid addition salts, are anti-tumor agents and, therefore, are useful in inhibiting the growth of various lymphomas, sarcomas, myelomas and leukemia cell lines. The ability of the compounds in treating tumors can be measured by the Tumor Cell Cytotoxicity test (TCC test) as follows:

In flat bottom microtiter plates (Nunc Roskieide, Denmark) are placed Abelson 8.1 tumor cells in DMEM +10% fetal calf serum and the tumor cell-containing plates are incubated with 1, 3, and 5 ug of the test compound for a period of 6 to 72 hours. The number of viable tumors cells can be determined by measuring the alkaline phosphatase in the following manner. The tumor cell plates are centrifuged (500×g.) for ten minutes and the supernatant flicked off. Without further washing, 100 $\mu$l of buffer containing 20 $\mu$l of diethanolamine, 2 uM of $MgCl_2.6H_2O$, 2.5 $\mu$M of p-nitrophenylphosphate and 10 mg Triton X-100 are added. The samples are incubated for 60 minutes at room temperature and the enzymatic reaction is terminated by the addition of 100 μl of 0.5N NaOH. The absorbance can then be measured at 405 nM using a Titertek Multiskan apparatus.

The anti-tumor activity of the compounds of formula I, and their pharmaceutically acceptable acid addition salts, may also be demonstrated employing the Influence on Cytotoxicity of ET-18—OCH₃ test (IC-ET test) as follows:

Bone marrow cell macrophages (10⁵/well) obtained from [BALB/CX57/BL6]F1 mice are incubated with 10 ug of (±)-1-octadecyl-2-methoxy-3-phosphoryl choline (ET-18—OCH₃) for 24 hours in flat bottom microtiter plates (Nunc Roskieide, Denmark), after which time they are centrifuged and washed once. Abelson 8.1 tumor cells in DMEM+10% fetal calf serum and 1, 3 and 5 ug of the test compound are then added to the plates. With the cytotoxicity of ET-18—OCH₃ (10 μg) alone set at 100%, the inhibition or enhancement of the cytotoxic effect, as measured by an alkaline phosphatase assay, can be determined and values recorded after 72 hours for 1, 3 and 5 ug of the test substance.

The usefulness of the compounds of formula I, and their pharmaceutically acceptable acid addition salts, in treating tumors may additionally be demonstrated employing the following procedure:

Meth A fibrosarcoma cells are induced in BALB/C mice by administering methylcholanthrene according to the procedure of Old, et al. (L. J. Old, E. A. Boyse, D. A. Clarke, and E. Carswell, Ann. N.Y. Acad. Sci., 101,: 80 (1962). These tumor cells are harvested from the peritoneal cavity 10 to 12 days after administration of methylcholanthrene. Ten CBF₁ mice of 10–12 week age are each implanted with $7.3 \times 10^6$ Meth A sarcoma cells to serve as control. A second group of ten CBF₁ mice are each implanted with $7.3 \times 10^6$ Meth A sarcoma cells and on day one after implant each mouse is treated p.o. with 5-50 ug of the test compound per day for a total of twenty or twenty-seven days. Tumor growth and survivors are assayed on days 7, 14, 21 and 28 after tumor implantation.

The precise dosage of a compound of formula I, or a pharmaceutically acceptable acid addition salt thereof, to be employed for inhibiting tumors depends upon several factors including the host, the nature and the severity of the condition being treated, the mode of administration and the particular compound employed. However, in general, satisfactory inhibition of tumors is achieved when a compound of formula I, or a pharmaceutically acceptable acid addition salt thereof, is administered orally or intravenously at a daily dosage of 1-100, preferably 5-35 mg/kg body weight or, for most larger primates, a daily dosage of 500-2000 mg, preferably 1000-1500 mg. A typical oral dosage is 400 mg, two to three times a day, or 20 mg/kg intravenously over a 24 hour period.

Usually, a small dosage is administered initially and the dosage is gradually increased until the optimal dosage for the host under treatment is determined. For parenteral administration, e.g., i.v., or i.p., a dosage somewhat lower than would be used for oral administration of the same compound to the same host having the same condition is usually employed. The upper limit of dosage is that imposed by side effects, and can be determined by trial for the host being treated, including humans.

A typical dosage unit for oral administration may contain 300 to 600 mg of a compound of formula I, or a pharmaceutically acceptable acid addition salt thereof. Preferred oral dosage units contain 300 to 500 mg, especially 350 to 450 mg of a compound of formula I, or a pharmaceutically acceptable acid addition salt thereof.

The compounds of formula I, and their pharmaceutically acceptable acid addition salts, may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositiions may be prepared by conventional means.

The compounds of formula I, and their pharmaceutically acceptable acid addition salts, may be formulated into such pharmaceutical compositions containing an amount of the active substance that is effective for inhibiting tumors, such compositions in unit dosage form and such compositions comprising a solid pharmaceutically acceptable carrier.

Tablets and capsules containing the ingredients indicated below may be prepared by conventional techniques and are useful as anti-tumor agents. The tablet may be administered two to four times a day whereas the capsule is suitably administered three times a day.

| Ingredients | Weight (mg) tablet | capsule |
|---|---|---|
| compound of formula I, e.g., the compound of Example 2 | 400 | 400 |
| tragacanth | 10 | — |
| lactose (spray-dried) | 197.5 | 250 |
| corn starch | 25 | — |
| talcum | 15 | — |
| magnesium stearate | 2.5 | — |
| Total | 650.0 | 650 |

The preferred pharmaceutical compositions from the standpoint of preparation and ease of administration are solid compositions, particularly liquid or hard-filled capsules and tablets containing from about 350 to 400 milligrams of the active ingredient.

The following examples show representative compounds encompassed by this invention and their synthesis. However, it should be clearly understood that they are for purposes of illustration only.

EXAMPLE 1

4-[2-(2-Methyl-1H-imidazol-1-yl)ethyl]-1-(1-oxoctadecyl)-piperidine

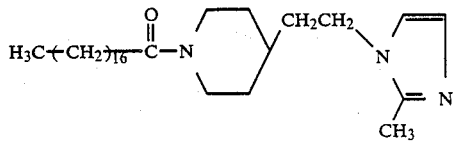

(a) Preparation of 4-[2-(2-methyl-1H-imidazol-1-yl)ethyl]pyridine

A stirred solution containing 52.5 g (0.50 mol) of 4-vinylpyridine, 36.9 g (0.45 mol) of 2-methylimidazole and 1.1 g of glacial acetic acid was heated to an internal temperature of 130° C. under a nitrogen atmosphere, maintained at this temperature for 5 hours, and then allowed to stand overnight at room temperature. The resultant solidified mass was dissolved in 150 ml of methylene dichloride, treated with charcoal, filtered through Celite and then concentrated in vacuo. The crude residue was crystallized from a mixture of methylene chloride and pentane in a ratio of 1:2.5 as the eluent to yield a solid.

(b) Preparation of 4-[2-(2-methyl-1H-imidazol-1-yl)ethyl]piperidine

A suspension containing 41.8 g (0.22 mol) of the compound prepared in (a) above, 450 ml of glacial acetic acid and 5.4 g of platinum oxide in a pressure bottle was affixed to a Parr Hydrogenation apparatus under 50 psi. of hydrogen and maintained at room temperature until the hydrogen uptake was completed. The reaction mixture was filtered through Celite, and the filter bed was then washed with approximately 100 ml of acetic acid. The combined filtrates were then concentrated in vacuo and the resultant residue was distilled in a Kugelrohr apparatus to yield a low melting white solid.

Preparation of the title compound

A stirred solution of 6.0 g (0.022 mol) of the compound prepared in (b) above and 3.30 g (0.033 mol) of triethylamine in a solvent mixture containing 80 ml of anhydrous toluene and 40 ml of anhydrous tetrahydrofuran under a nitrogen atmosphere was treated, dropwise, with a solution of 7.8 g (0.026 mol) of stearoyl chloride in 20 ml of toluene and the resultant mixture was stirred at room temperature for 2 days. The resultant solids were filtered and the filtrate was concentrated in vacuo. The crude residue was dissolved in 150 ml of methylene chloride, washed once with 100 ml of 2N sodium hydroxide, washed twice with 200 ml of water, dried over anhydrous magnesium sulfate, filtered and concentrated in vacuo. The semi-gummy solid obtained was then distilled in a Kugelrohr apparatus to yield the title compound.

TCC test—98.9% inh. at 5 µg
IC-ET test—98.5% enh. at 5 µg

EXAMPLE 2

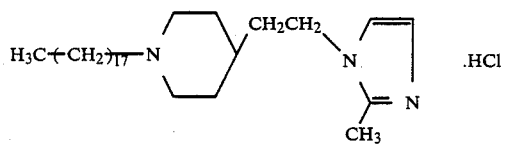

A stirred suspension of 0.684 g (0.009 mol) of lithium aluminum hydride in 115 ml of anhydrous tetrahydrofuran under a nitrogen atmosphere was cooled in an ice bath and treated, dropwise, with a solution of 4.0 g (0.009 mol) of the compound of Example 1 in 50 ml of tetrahydrofuran over a period of 15 minutes. The reaction mixture was then refluxed for 8 hours, cooled in a ice bath and treated, dropwise, successively with 1 ml of saturated sodium chloride, 1 ml of 2N sodium hydroxide and 2 ml of water, after which time it was allowed to stand overnight at room temperature. The resultant solids were filtered, and the filter cake was washed with tetrahydrofuran. The combined filtrates were then concentratd in vacuo to obtain an oil which was distilled in a Kugelrohr apparatus to yield the free base form of the above compound.

A solution of 3.0 g of the free base in ethanol was cooled in an ice bath and treated with anhydrous hydrogen chloride gas. The salt was then filtered off and dried to obtain the title compound, m.p. 263°–265° C.

TCC test—98.7% inh. at 5 µg
IC-ET test—98.5% enh. at 5 µg

EXAMPLE 3

Following essentially the procedure of Example (1a) above, and using in place of the 2-methyl-imidazole, an approximately equivalent amount of:

(a) 2-undecylimidazole
(b) 2-ethylimidazole; and
(c) 2-isopropylimidazole;

there was obtained (A) 4-[2-(2-undecyl-1H-imidazol-1-yl)ethyl]pyridine;
(B) 4-[2-(2-ethyl-1H-imidazol-1-yl)ethyl]pyridine; and
(C) 4-[2-(2-isopropyl-1H-imidazol-1-yl)ethyl]pyridine, respectively.

EXAMPLE 4

Following essentially the procedure of Example (1a) above, and using in place of the 4-vinylpyridine, an approximately equivalent amount of 2-vinylpyridine, there was obtained 2-[2-(2-methyl-1H-imidazol-1-yl)ethyl]pyridine.

EXAMPLE 5

Following essentially the procedure of Example (1b) above, and using in place of 4-[2-(2-methyl-1H-imidazol-1-yl)ethyl]pyridine, an approximately equivalent amount of the compounds of Examples (3A)–(3C) and Example 4, there was obtained (A) 4-[2-(2-undecyl-1H-imidazol-1-yl)ethyl]piperidine;
(B) 4-[2-(2-ethyl-1H-imidazol-1-yl)ethyl]piperidine;
(C) 4-[2-(2-isopropyl-1H-imidazol-1-yl)ethyl]piperidine; and
(D) 2-[2-(2-methyl-1H-imidazol-1-yl)ethyl]piperidine, respectively.

EXAMPLE 6

1-(1-Oxo-2,2-dimethylpropanyl)-4-[2-(2-undecyl-1H-imidazol-1-yl)ethyl]piperidine

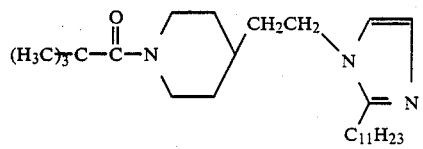

Following essentially the last step of the procedure for preparing the compound of Example 1, and using in place of 4-[2-(2-methyl-1H-imidazol-1-yl)ethyl]piperidine and stearoyl chloride, approximately equivalent amounts of the compound of Example (5A) and pivaloyl chloride, respectively, the title compound was obtained as an oil.

TCC test—98.8% inh. at 5 µg
IC-ET test—99.7% enh. at 5 µg

EXAMPLE 7

1-(1-Oxohexanyl)-4-[2-(2-undecyl-1H-imidazol-1-yl)ethyl]piperidine

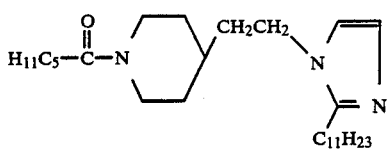

Following essentially the last step of the procedure for preparing the compound of Example 1, and using in place of 4-[2-(2-methyl-1H-imidazol-1-yl)ethyl]piperidine and stearoyl chloride, approximately equivalent amounts of the compound of Example (5A) and hexanoyl chloride, respectively, the title compound was obtained as a liquid, b.p. 167°–170° C.

TCC test—98.7% inh. at 5 μg
IC-ET test—99.8% enh. at 5 μg

EXAMPLE 8

4-[2-(2-methyl-1H-imidazol-1-yl)ethyl]-1-(1-oxo-hexadecanoyl)piperidine

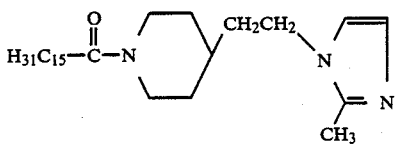

Following essentially the last step of the procedure for preparing the compound of Example 1, and using in place of stearoyl chloride, an approximately equivalent amount of hexadecanoyl chloride, the title compound was obtained, m.p. 112° to 115° C.

TCC test—99.0% inh. at 5 μg
IC-ET test—99.0% enh. at 5 μg

EXAMPLE 9

4-[2-(2-ethyl-1H-imidazol-1-yl)ethyl]-1-(1-oxohexadecanoyl)piperidine

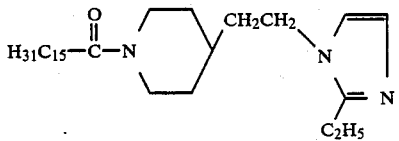

Following essentially the last step of the procedure for preparing the compound of Example 1, and using in place of 4-[2-(2-methyl-1H-imidazol-1-yl)ethyl]piperidine and stearoyl chloride, approximately equivalent amounts of the compound of Example (5B) and hexadecanoyl chloride, respectively, the title compound was obtained as a liquid, b.p. 127°–135° C.

TCC test—98.3% inh. at 5 μg
IC-ET test—97.5% enh. at 5 μg

EXAMPLE 10

4-[2-(1H-imidazol-1-yl)ethyl]-1-(1-oxoctadecyl)-piperidine

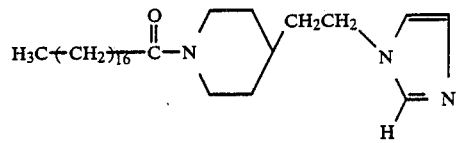

(a) Preparation of 4-[2-(1H-imidazol-1-yl)ethyl]pyridine

Following essentially the procedure of Example (1a) above, and using in place of the 2-methylimidazole, an approximately equivalent amount of imidazole, a solid was obtained.

(b) Preparation of 4-[2-(1H-imidazol-1-yl)ethyl]piperidine

Following essentially the procedure of Example (1b) above, and using in place of the compound of Example (1a), an approximately equivalent amount of the compound prepared in (a) above, a solid was obtained.

Preparation of the title compound

Following essentially the last step of the procedure for preparing the compound of Example 1, and using in place of 4-[2-(2-methyl-1H-imidazol-1-yl)ethyl]piperidine, an approximately equivalent amount of the compound prepared in (b) above, the title compound was obtained, m.p. 65°–67° C.

TCC test—87.5% inh. at 5 μg
IC-ET test—98.5% enh. at 5 μg

EXAMPLE 11

2-[2-(2-methyl-1H-imidazol-1-yl)ethyl]-1-(oxoctadecyl)piperidine

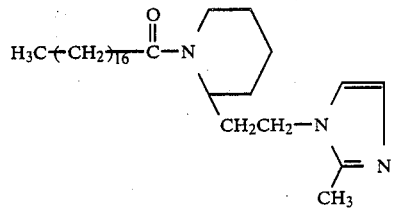

Following essentially the last step of the procedure for preparing the compound of Example 1, and using in place of 4-[2-(2-methyl-1H-imidazol-1-yl)ethyl]piperidine, an approximately equivalent amount of the compound of Example (5D), the title compound was obtained as an oil.

TCC test—96.5% inh. at 5 μg
IC-ET test—93.0% enh. at 5 μg

EXAMPLE 12

Following essentially the procedure for preparing the compound of Example 2 with the exception of the formation of the hydrochloride acid addition salt, and using in place of the compound of Example 1, an approximately equivalent amount of:
(a) the compound of Example 7; and
(b) the compound of Example 9;
there was obtained (A) 1-hexyl-4-[2-(2-undecyl-1H-imidazol-1-yl)ethyl]-piperidine;
TCC test—99.0% inh. at 5 ug
IC-ET test—98.8% enh. at 5 ug
and
(B) 4-[2-(2-ethyl-1H-imidazol-1-yl)ethyl]-1-hexadecyl-piperidine,
TCC test—98.5% inh. at 5 ug
IC-ET test—99.2% enh. at 5 ug,
respectively.

EXAMPLE 13

1-dodecyl-4-[2-(2-methyl-1H-imidazol-1-yl)ethyl]-piperidine dihydrochloride

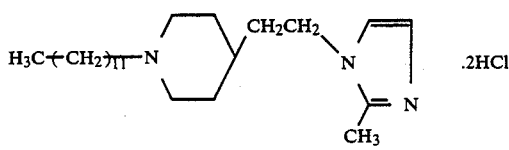

(a) Preparation of 4-[2-(2-methyl-1H-imidazol-1-yl)ethyl]-1-(1-oxododecyl)-piperidine Following essentially the last step of the procedure for preparing the compound of Example 1, and using in place of stearoyl chloride, an approximately equivalent amount of dodecanoyl chloride, a solid was obtained.

Preparation of the title compound

Following essentially the procedure for preparing the compound of Example 2, ad using in place of the compound of Example 1, an approximately equivalent amount of the compound prepared in (a) above, the title compound was obtained, m.p. 243°–245° C.
TCC test—98.8% inh. at 5 μg
IC-ET test—98.6% enh. at 5 μg

EXAMPLE 14

Following essentially the procedure for preparing the compound of Example 2, and using in place of the compound of Example 1, an approximately equivalent amount of:
(a) the compound of Example 8;
(b) the compound of Example 10; and
(c) the compound of Example 11;
there was obtained
(A) 1-hexadecyl-4-[2-(2-methyl-1H-imidazol-1-yl)ethyl]piperidine sesquihydrochloride, m.p. 112°–115° C.,
TCC test—99.0% inh. at 5 μg
IC-ET test—98.6% enh. at 5 μg;
(B) 4-[2-(1H-imidazol-1-yl)ethyl]-1-octadecylpiperidine dihydrochloride, m.p. 218° C.,
TCC test—99.0% inh. at 5 μg
IC-ET test—99.0% enh. at 5 μg;
and
(C) 2-[2-(2-methyl-1H-imidazol-1-yl)ethyl]-1-octadecyl-piperidine dihydrochloride, m.p. 130° C.,
TCC test—99.0% inh. at 5 μg
IC-ET test—99.0% enh. at 5 μg,
respectively.

EXAMPLE 15

1-Hexadecyl-4-[2-(2-isopropyl-1H-imidazol-1-yl)ethyl]-piperidine dihydrochloride

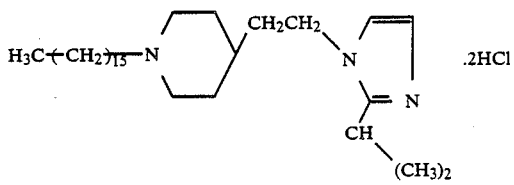

(a) Preparation of 4-[2-(2-isopropyl-1H-imidazol-1-yl)ethyl]-1-(1-oxohexadecyl)-piperidine Following essentially the last step of the procedure for preparing the compound of Example 1, and using in place of 4-[2-(2-methyl-1H-imidazol-1-yl)ethyl]piperidine and stearoyl chloride, approximately equivalent amounts of the compound of Example (5C) and hexadecanoyl chloride, respectively, a solid was obtained.

Preparation of the title compound

Following essentially the procedure for preparing the compound of Example 2, and using in place of the compound of Example 1, an approximately equivalent amount of the compound prepared in (a) above, the title compound was obtained, m.p. 213°–215° C.
TCC test—98.5% inh. at 5 μg
IC-ET test—98.7% enh. at 5 μg.

What is claimed is:

1. A compound of formula I:

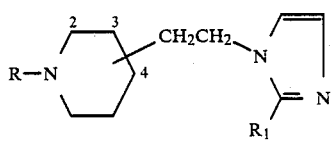

wherein
R is a group selected from

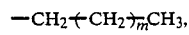

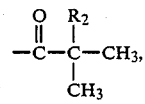

where m is an integer 2 to 18 and $R_2$ is hydrogen or methyl; and $R_1$ is $-(CH_2)_n R_3$, where n is 0 or an integer 1 to 13, and $R_3$ is hydrogen, i-propyl or t-butyl, and the floating group is in the 2- or 4-position, with the provisos that: (1) the sum of the carbon atoms in $R_1$ does not exceed 13; and (2) the sum of the carbon atoms in R and $R_1$ does not exceed 25;

or a pharmaceutically acceptable acid addition salt thereof.

2. A compound according to claim 1 of formula I':

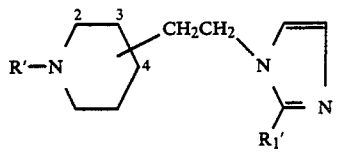

wherein
R' is a group selected from

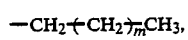

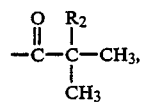

where m' is an integer 4 to 16 and $R_2$ is as defined in claim 1; and $R_1$ is $-(CH_2)_{\overline{n}}R_3$, where n' is 0 or an integer 1 to 11, and $R_3$ is as defined in claim 1, and the floating group is in the 2- or 4-position, with the provisos that: (1) the sum of the carbon atoms in $R_1$ does not exceed 11; and (2) the sum of the carbon atoms in R' and $R_1$ is between 15 and 25;

or a pharmaceutically acceptable acid addition salt thereof.

3. A compound according to claim 2 wherein R' and $R_1$ are as defined in claim 2, with the provisos that: (1) the sum of the carbon atoms in $R_1$ does not exceed 11; and (2) the sum of the carbon atoms in R' and $R_1$ is between 15 and 20; or a pharmaceutically acceptable acid addition salt thereof.

4. A compound according to claim 3 having the formula

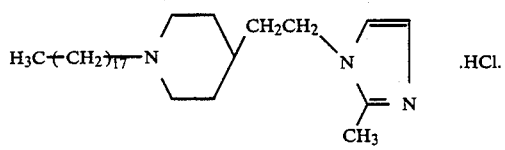

5. A compound according to claim 3 having the formula

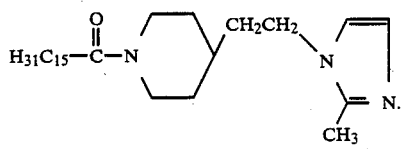

6. A compound according to claim 3 having the formula

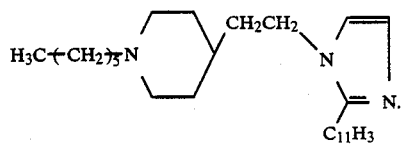

7. A compound according to claim 3 having the formula

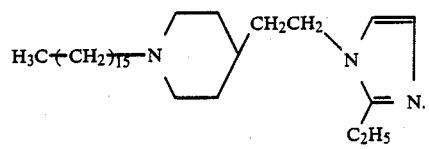

8. A compound according to claim 3 having the formula

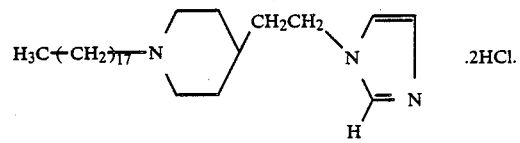

9. A compound according to claim 3 having the formula

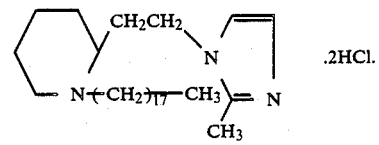

10. A method of treating tumors comprising administering to a subject afflicted therewith a therapeutically effective amount of a compound according to claim 1, or a pharmaceutically acceptable acid addition salt thereof.

11. A method according to claim 10 comprising administeringg a therapeutically effective amount of a compound having the formula

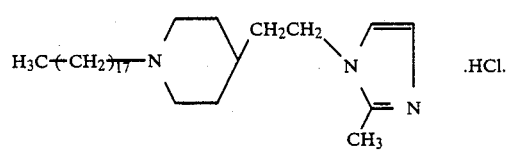

12. A method according to claim 10 comprising administering a therapeutically effective amount of a compound having the formula

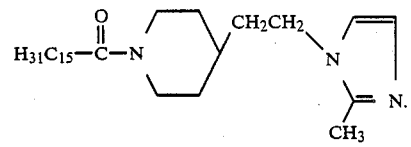

13. A method according to claim 10 comprising administering a therapeutically effective amount of a compound having the formula

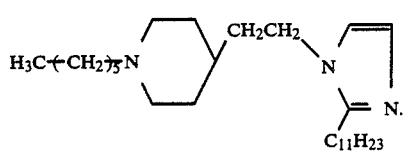

14. A method according to claim 10 comprising administering a therapeutically effective amount of a compound having the formula

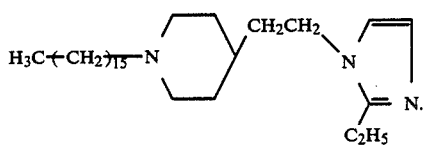

15. A method according to claim 10 comprising administering a therapeutically effective amount of a compound having the formula

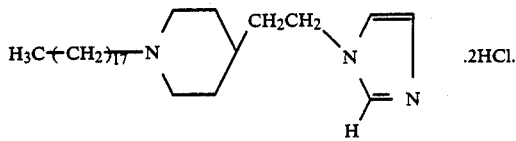

16. A method according to claim 10 comprising administering a therapeutically effective amount of a compound having the formula

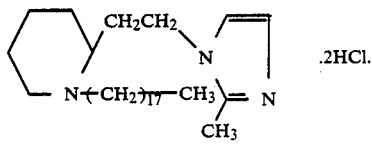

17. A pharmaceutical composition useful in treating tumors comprising a pharmaceutically acceptable carrier and a therapeutically effective amount of a compound of claim 1, or a pharmaceutically acceptable acid addition salt thereof.

* * * * *